United States Patent
Mazzoni

(10) Patent No.: US 7,214,209 B2
(45) Date of Patent: May 8, 2007

(54) DISPENSER

(75) Inventor: Paolo Mazzoni, Milan (IT)

(73) Assignee: Glaxo Group Limited, Greenford, Middlesex (GB)

( * ) Notice: Subject to any disclaimer, the term of this patent is extended or adjusted under 35 U.S.C. 154(b) by 759 days.

(21) Appl. No.: 10/474,489

(22) PCT Filed: Apr. 10, 2002

(86) PCT No.: PCT/GB02/01690

§ 371 (c)(1),
(2), (4) Date: Oct. 8, 2003

(87) PCT Pub. No.: WO02/083219

PCT Pub. Date: Oct. 24, 2002

(65) Prior Publication Data

US 2004/0138618 A1 Jul. 15, 2004

(30) Foreign Application Priority Data

Apr. 10, 2001 (GB) .................. 0109001.8

(51) Int. Cl.
*A61M 37/00* (2006.01)
*A61M 1/00* (2006.01)
(52) U.S. Cl. ...................... 604/131; 604/151
(58) Field of Classification Search .................. 604/61, 604/62, 64, 131–135, 140–143, 145–155
See application file for complete search history.

(56) References Cited

U.S. PATENT DOCUMENTS

| 3,543,966 | A | * | 12/1970 | Shapero et al. ................ 222/94 |
| 5,137,516 | A | | 8/1992 | Rand et al. |
| 5,143,084 | A | * | 9/1992 | Macemon et al. .......... 600/584 |
| 5,330,431 | A | * | 7/1994 | Herskowitz ................. 604/153 |
| 5,408,994 | A | * | 4/1995 | Wass et al. ............ 128/203.15 |
| 5,478,316 | A | * | 12/1995 | Bitdinger et al. ........... 604/135 |
| 5,814,020 | A | * | 9/1998 | Gross .......................... 604/141 |
| 6,099,503 | A | * | 8/2000 | Stradella ..................... 604/135 |
| 6,186,141 | B1 | * | 2/2001 | Pike et al. ............. 128/203.12 |
| 6,530,900 | B1 | * | 3/2003 | Daily et al. ................. 604/132 |
| 6,669,668 | B1 | * | 12/2003 | Kleeman et al. ............ 604/131 |
| 6,692,469 | B1 | * | 2/2004 | Weekes et al. .............. 604/197 |

FOREIGN PATENT DOCUMENTS

EP 0 546 607 A 6/1993
WO WO 97/42992 11/1997

* cited by examiner

Primary Examiner—Nicholas D. Lucchesi
Assistant Examiner—Matthew DeSanto
(74) Attorney, Agent, or Firm—J. Michael Strickland

(57) ABSTRACT

A dispensing apparatus for dispensing a unit dose of a pharmaceutical substance, in particular one for intranasal administration, is disclosed. The unit dose is contained in a cylinder which is moved relative to a piston to expel the contents thereof through a passage in the piston and out of a nozzle opening. The dispensing apparatus includes a case with a base part and a cover.

23 Claims, 15 Drawing Sheets

DISPENSER

This application is filed pursuant to 35 U.S.C. § 371 as a United States National Phase Application of International Patent Application Ser. No. PCT/GB02/01690 filed Apr. 10, 2002, which claims priority from Great Britain Application No. 0109001.8 filed in the United Kingdom on Apr. 10, 2001.

The present invention relates to a device for dispensing a pharmaceutical substance. In particular, the invention relates to a device for dispensing a pharmaceutical substance by intranasal administration.

European Patent Publication No. EP-A-0546607 in the name of Glaxo Group Limited discloses a dispenser for manual discharge of a single dose of a flowable substance. The device consists of a casing with a nozzle member and shoulders to the sides of the nozzle member. The nozzle member has a piston extending inwardly from an outlet opening, the piston having at least one discharge channel. A vial of the pharmaceutical substance to be dispensed is mounted on the piston member with a stopper arranged across the vial to seal in the substance. The piston includes a hollow needle, so that on pressing of the vial onto the piston member, the stopper is pierced by the needle to allow the substance to be expelled through the discharge channel and out of the nozzle opening. The described device is a one-use only device and is intended to be discarded after use.

International Patent Publication No. WO97/42992 in the name of Glaxo Wellcome Australia Limited discloses a device for dispensing a unit dose of a pharmaceutical substance. The device includes a body member which has a discharge system which can be operated by the user to effect discharge of the pharmaceutical substance, in particular by means of a spring loaded air piston which injects air into a container of the substance to discharge it. A number of nozzle assemblies are provided, each nozzle assembly including a container of a unit dose of the pharmaceutical substance. A single nozzle assembly is mounted on the body member and in one embodiment a driving spring for the air piston is loaded with spring energy by the action of mounting the nozzle assembly on the body. After the spring is released, and the substance thus discharged, the nozzle assembly is discarded and a fresh nozzle assembly can be mounted on the body as required.

U.S. patent Publication No. U.S. Pat. No. 5,137,516 again in the name of Glaxo Group Limited describes a device for administering a dose of a pharmaceutical substance, in particular by self-injection by the user. The device holds a syringe of the pharmaceutical substance and the syringe is pressed against the user's skin by a spring force, the spring force being released by relative movement of cooperating sleeves of the device and by pressure on a button on one end of the device. The spring can be placed into a ready-to-use state by loading of the syringe onto the device. The device may be provided in a carry case, along with a small number of spare syringes.

There remains a need for a pharmaceutical dispensing device which is easy and convenient to use.

According to the invention there is provided a device for dispensing a pharmaceutical substance comprising:

a base member and a cover member closeable thereon;

a dispensing member which is movable between a first position on the base member under the closed cover member and a second position protruding from the base member after opening and reclosing of the cover member;

a container of the pharmaceutical substance to be dispensed;

an actuating member for discharging the pharmaceutical substance from the container and through the dispensing member;

wherein in the second position of the dispensing member the container is in registration with the actuating member so that the release member can cause dispensing of the pharmaceutical substance through the dispensing member.

Preferably, the dispensing member includes the container and the dispensing member is removable from the base member for disposal after use.

The dispensing member is preferably pivotable relative tithe base between the first and second position.

The dispensing member can have a protective cap which has locking wings to hold it on the dispensing member, the locking wings being retracted upon mounting of the dispensing member on the base.

The base member preferably has an edge surface which prevents registration of the dispensing member with the actuating member until removal of the protective cap.

The actuating member has a primed condition and an unprimed condition, and the primed condition can be achieved by sliding movement of a carriage on the base member.

The cover member advantageously cooperates with the carriage such that after dispensing, opening of the cover member slides back the carriage to its initial position.

A push button on the base or cover member can move the release member, inclined surfaces on the release member then moving catches on the base member which hold the actuating member.

A preferred embodiment of the invention is described in more detail below, by example only, with reference to the accompanying drawings.

Figure 1:
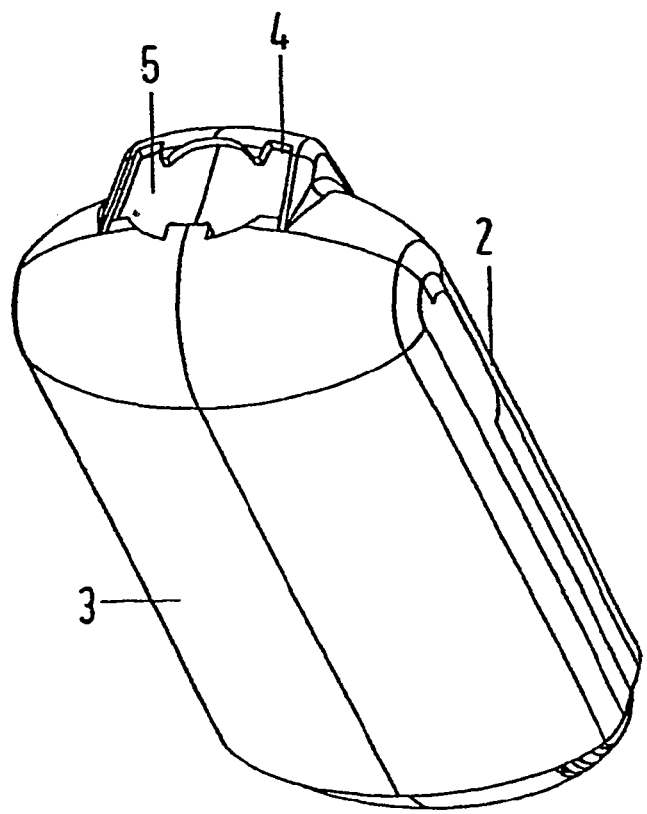
FIG. 1 is a perspective view of a device for dispensing a pharmaceutical substance in accordance with an embodiment of the invention, in a closed condition.

The perspective view of FIG. 1 shows a device 1 for dispensing a pharmaceutical substance, the device being in the form of a carry case of a generally parallelepiped shape, the edges, ends and upper and lower surfaces of the parallelepiped shape being rounded.

The carry case includes a base member 2 and a cover member 3, these members being hingedly connected to one another at the lower end of the device as seen in FIG. 1. At the upper end of the device as seen in FIG. 1, where the base 2 and cover 3 move apart from each other, an opening 4 is provided in the end of the base, this opening 4 being closed by a lid 5 which is mounted on the cover 3.

Lifting of the cover 3 from the base 2, and thus opening of the device, is achieved by squeezing together the sides of the cover 3.

Figure 2:
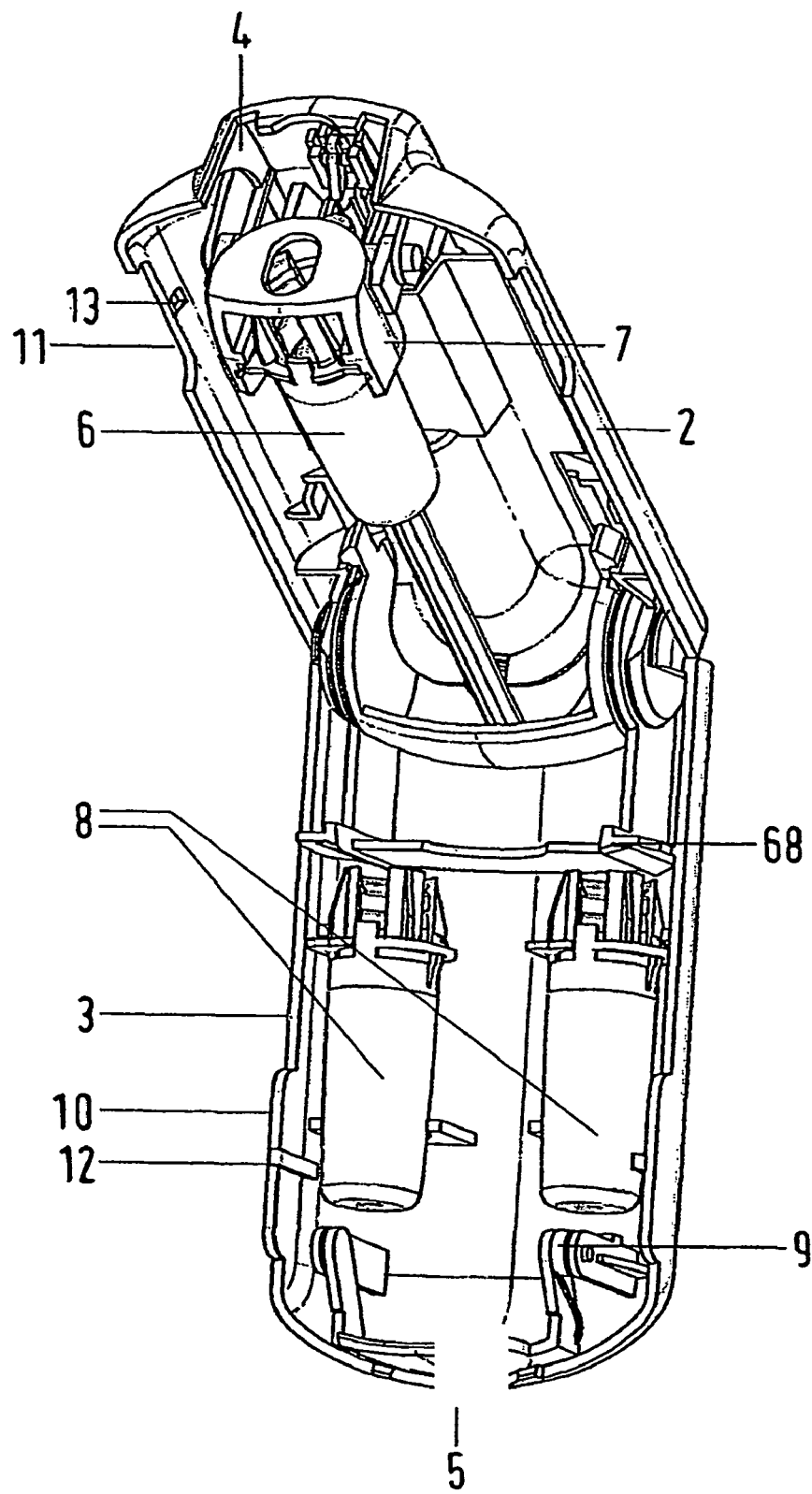
FIG. 2 is a perspective view of the device of FIG. 1 in an open condition.

The open condition of the device is shown in the perspective view of FIG. 2. In this Figure it can be seen that the cover 3 is pivoted away from the base 2. A unit 6 which contains the pharmaceutical substance to be dispensed is mounted on a support 7 which in turn is pivotally mounted on the base 2. In this embodiment, where the pharmaceutical substance is intended for nasal administration, the unit 6 is of a generally cylindrical shape with dimensions appropriate for insertion into the user's nasal cavity, after removal of a protective cover. In view of its shape and function, the unit 6 which contains the pharmaceutical substance is referred to in the following description as a nozzle unit.

On the cover 3 are arranged spare nozzle units 8, each of these being identical to the nozzle unit 6 mounted on the base 2 by means of the support 7.

The lid 5 which closes the end opening 4 of the base 2 is seen at the bottom of FIG. 2. Lid 5 is arranged on the cover 3 by means of a pivotal mounting 9.

The means by which the cover is opened and closed, relative to the base, are visible in the perspective view of FIG. 2. Curved portions 10 extend from the sides of the cover 3 and locate in correspondingly shaped recesses 11 in the sides of the base 2. A catch 12 on the curved portion 10 locates in a catch recess 1 on the inside of the cover, immediately adjacent the recess 13. Upon closing of the cover on the base, due to the inherent resilience of the material from which the cover is formed, the catch 12 locates in the catch recess 11. Opening of the cover 3 is achieved by squeezing together the sides of the cover, at the curved portions 10, thus releasing the catch 12. The arrangement of the catch and catch recess is of course present on both sides of the device.

Figure 3A:
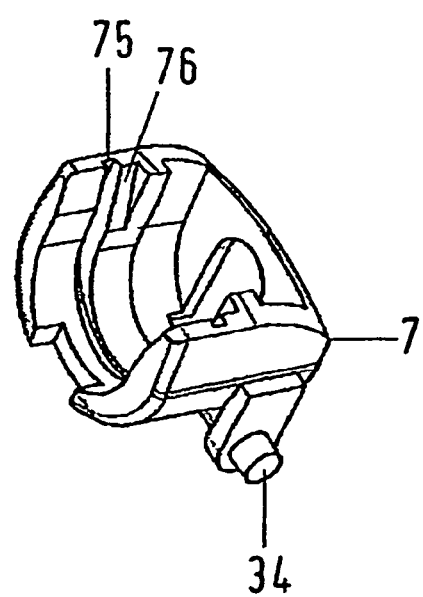
FIG. 3a is a perspective view of a part of FIG. 3, but at a larger scale.
Figure 3:
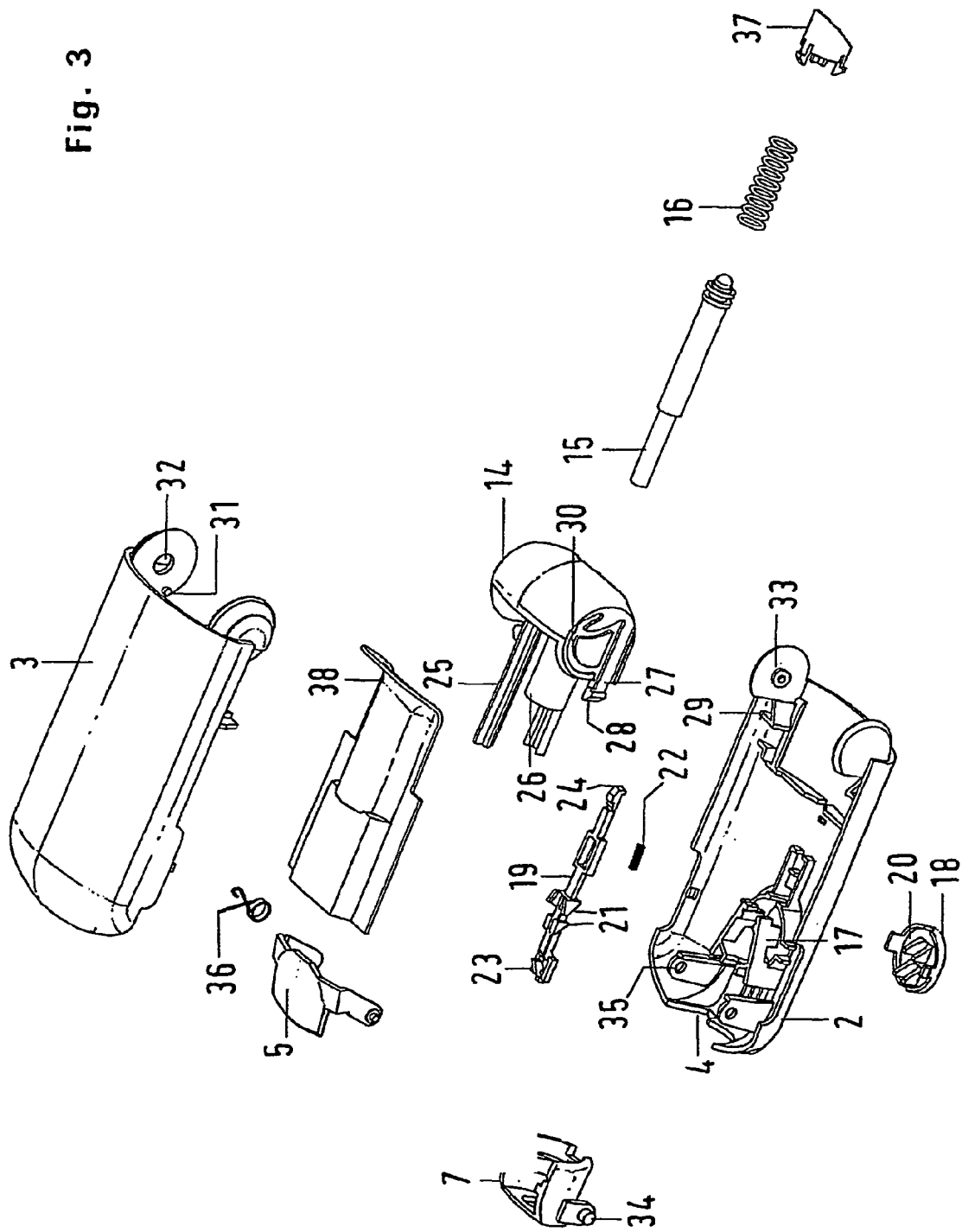
FIG. 3 is an exploded perspective view of the device of FIGS. 1 and 2, but omitting the unit which contains the pharmaceutical substance to be dispensed.

The construction of the base and the cover, and the component parts thereof, are clearly shown in the exploded perspective view of FIG. 3. This Figure does not, however, show the nozzle unit 6 or the spare nozzle unite 8. In FIG. 3, the cover 3 is shown separated and above the base 2. The pivoting support unit 7 is seen to the left of base 2. Carriage 14 is also seen above the base 2, this carriage normally being arranged on base 2 for sliding movement between a first, rearward position and a second, advanced position. Piston rod 15 is also normally mounted on the base, and this piston rod 15 can be driven by the force of piston spring 16 to urge the pharmaceutical substance from the nozzle unit 6, upon actuation of the dispensing device.

The piston rod 15 is maintained in a non-dispensing position by resilient arms 17 on the inside of the base 2. Actuation of the device, and thus release of the piston rod 15, occurs by means of pressure on a button 18 located in the base 2, button 18 cooperating with a shuttle 19. Inclined surfaces 20 on the button 18 act on inclined surfaces 21 of the shuttle 19 to move the shuttle 19 along the base, this movement opening the arms 17 to release the piston rod 15, as will be described in more detail below. The shuttle 19 moves against the action of shuttle spring 22.

The shuttle 19 is initially held against movement along the base by a first safety catch 23 and a second safety catch 24. The purposes of the safety catch catches are to ensure that the dispensing device is properly and safely used. The full purpose of these safety features will be described below.

The carriage 14 includes a blocking arm 25, which blocks forward movement of the carriage when a nozzle unit is mounted on the support 7 and pivoted inside the device 1 (i.e. in the position seen in FIG. 2). The carriage 14 also includes piston rod housing 26 through which the piston rod 15 extends. At each side of the carriage 14 is a catch arm 27 at the forward end of which there is a hook catch 28. The catches 28 engage over shoulders 29 on the base 2, when the carriage 14 is mounted in a rearward position on the base 2.

On each side of the carriage 14, adjacent the catch arms 27 there is arranged a cam track 30. A pin 31 at each inner side of the pivoting end of cover 3 moves around the cam track 30 in a manner to be described below. The pivoting end of the cover 3 includes apertures 32 which locate over pivot lugs 33 on the base 2, to allow pivotal movement of the cover relative to the base 2.

Pivoting lugs 34 are provided on the support 7, these lugs 34 locating in pivot apertures 35 at the forward end of the base 2. Thus, the support 7 can pivot about the base, between a position facing inwardly of the base and a position facing outwardly of the base. In the outer position the support 7 locates in the opening 4 of the base.

Cover spring 36 is fitted on the cover, to urge the lid 5 into a position closing the opening 4 when the support 7 is folded inside the base. When the support 7 is folded out of the base, obviously the lid 5 cannot cover the opening 4 and in this situation, when the cover is closed on the base, the lid 5 is folded back inside the cover, against the action of cover spring 36.

A plug 37 is provided to close the end of the passage through the piston housing 26 of the carriage 14. The end of the passage is not visible in FIG. 3, but it can be explained here that the piston rod 15 and piston spring 16 are mounted in the carriage 14 by insertion through the outer end of the carriage, the opening in the carriage then being closed by the plug 37.

An inner cover plate 38 is provided between the base 2 and the cover 3. The cover plate 38 is mounted on the base to conceal the operating parts of the actuating mechanism, in particular the shuttle 19, spring arms 17 and inner surfaces of the button 18.

The support 7 is shown in more detail in the enlarged perspective view of FIG. 3a. The support 7 is shaped so as to snugly receive the nozzle unit 6. Correct mounting of the nozzle unit 6 is ensured by means of a groove 75 which curves around the inside of the support. Immediately adjacent the groove 75 are opposing inclined surfaces 76 which approach each other as they extend into the support. The purpose of groove 75 and surfaces 76 will be explained shortly.

Figure 4A:
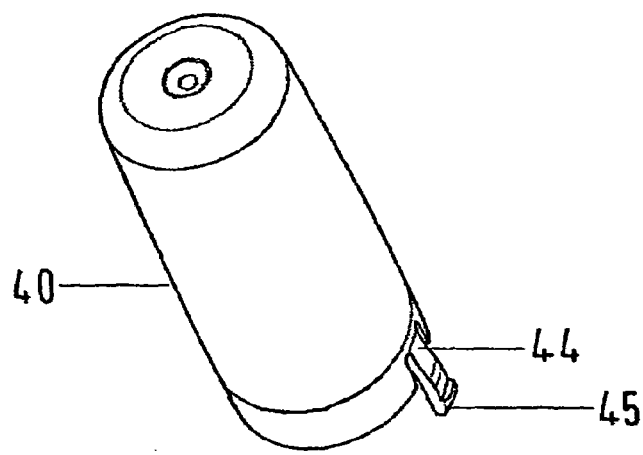
FIGS. 4a and 4b are perspective views of the unit which contains the pharmaceutical substance, FIG. 4a being a partly exploded view.
Figure 4B:
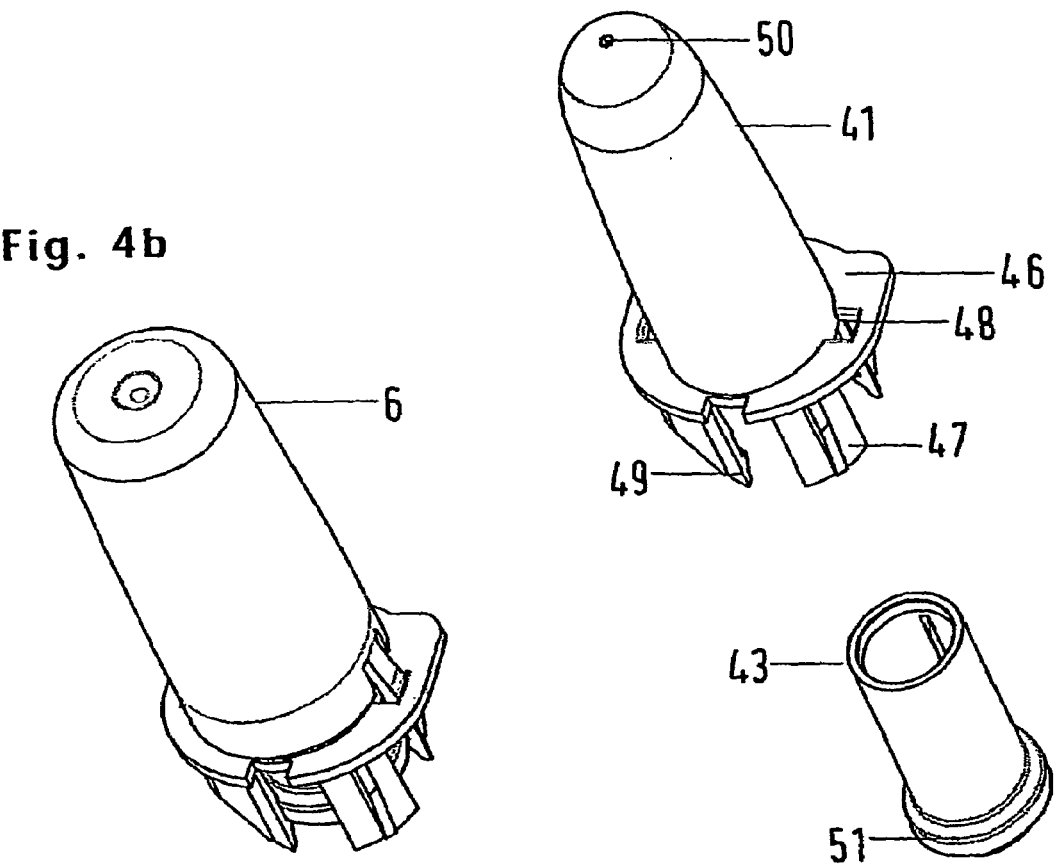

FIGS. 4a and 4b show the nozzle unit 6 which in FIG. 2 is shown mounted on the pivoting support 7. The nozzle unit 6 includes a cap 40, a nozzle member 41 and a vial holder 43 which holds a vial of the pharmaceutical substance to be dispensed (the vial not being visible in this Figure). At each side of the cap 40 are cap wings 44 and at the end of each wing there is a protruding part 45 which forms a cap wing catch. The nozzle member 41 has a skirt 46 extending laterally therefrom, the skirt having skirt legs 47 and skirt openings 48. The cap wings 44 are resilient and upon location of the cap 40 over the nozzle member 41 the cap wings 44 locate in the skirt openings 48, with the cap wing catches 45 clipping under the skirt to prevent removal of the cap 40 from the nozzle member 41.

The skirt legs 47 include, on their inner surfaces, a circumferential groove 49. At the forward end of the nozzle member 41 there is a nozzle opening 50, through which the pharmaceutical substance is dispensed after the nozzle member is inserted in the user's nasal cavity.

The skirt 46 has a rounded shape on one side which matches the curved shape of the groove 75 of the support 7. This matching of shape ensures that the nozzle unit can only be inserted into the support in one predetermined orientation. Upon insertion, the skirt 46 fits in the groove 75 and the cap wings 44 will be forced along the surfaces 76 which will tend to draw the cap wings 44 closer together.

The vial holder 43 is of a generally cylindrical shape and locates within the nozzle member 41. A circumferential rim 51 at the base of the vial holder 43 locates in the circumferential groove 49 of the skirt legs 47 in order that the vial holder can be securely held within the nozzle member 41. The skirt legs have a degree of resiliency so that the vial holder can be pushed further within the nozzle member 41 by an appropriate force.

It can be mentioned at this point that the inner construction and the working of the nozzle member is, in this embodiment, exactly as described in European patent application number EP-A-0546607. Thus the way in which the pharmaceutical substance is held within the nozzle member, and the way in which it is dispensed, need not be described in detail here. It can, however, be noted that the vial holder 43 in the present device is shorter than the equivalent member in EP-A-0546607. In the present case, it can be seen that the vial holder does not extend beyond the ends of the skirt legs 47, so that accidental pressure on the vial holder 43, when the nozzle units are handled by the user, is avoided, the skirt legs 47 surrounding and protecting the end of the vial holder 43.

Figure 5A:
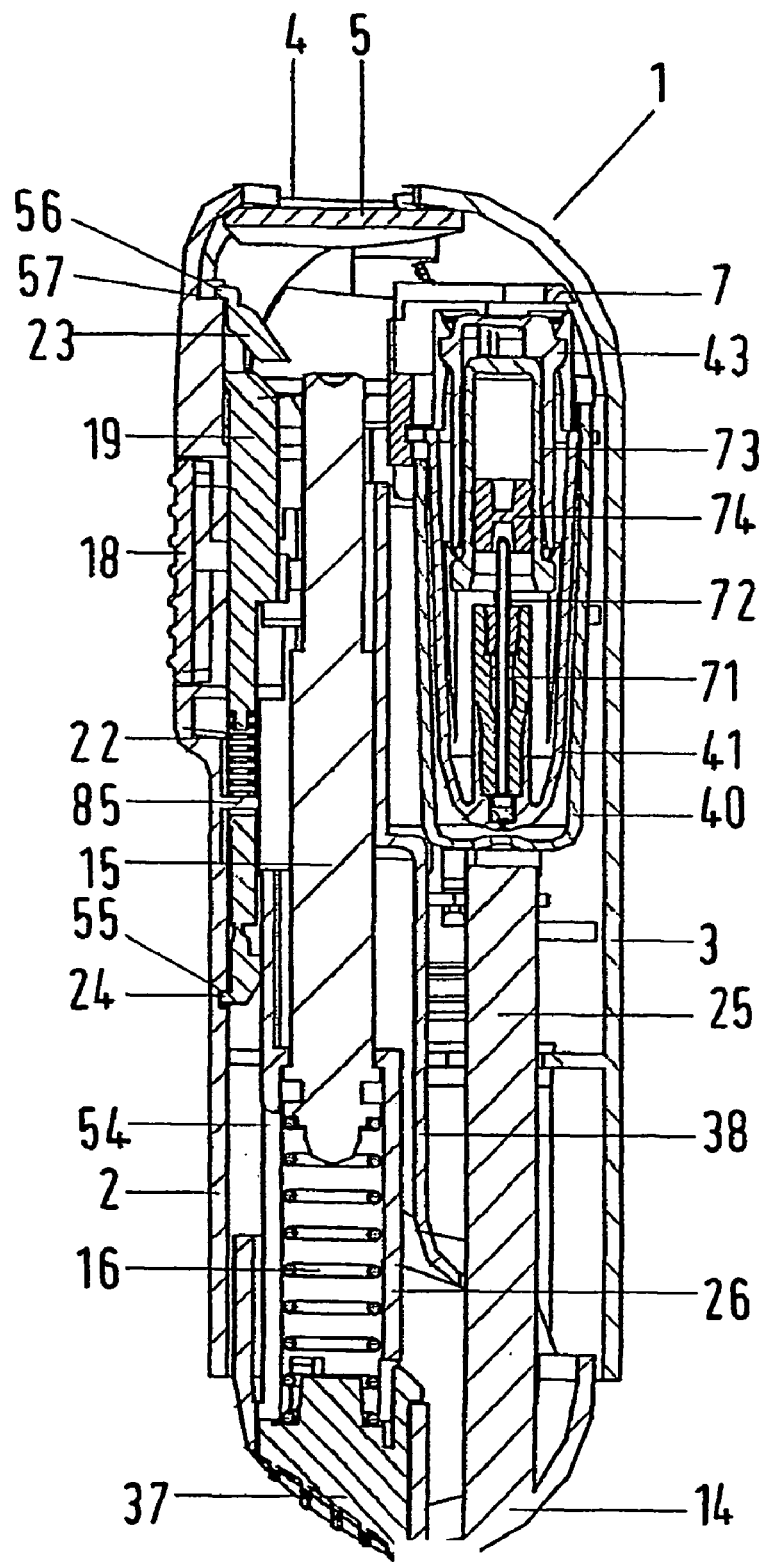
FIGS. 5a and 5b are vertical and horizontal sectional views of the device, showing the unit containing the pharmaceutical substance in its inner position.

The vertical cross-sectional view of FIG. 5a shows the device in a closed condition, with the cover 3 closed onto the base 2, the lid 5 closing the opening 4. The support 7 with a nozzle unit 6, mounted thereon is folded inside the device. As clearly seen in this Figure, the end of the blocking arm 25 of the carriage 14 is adjacent the end of the pivot unit 6, thus blocking movement of the carriage 14 along the base 2. Piston rod 15 is seen mounted within the piston housing 26 of the carriage, the end of the carriage housing 26 being closed by the plug 37.

One side of the piston housing 26 has an open portion 54 into which one end of the shuttle 19 can move, when the carriage is advanced. FIG. 5a shows the shuttle catch 24 of the shuttle 19 located in a catch recess 55 in the base 2, the holding of the catch 24 in the recess being against the force of the inherent resiliency of the end portion of the shuttle 19. Accordingly, when the carriage is in such a position that the open portion 54 of the piston support 26 is next to the shuttle catch 24, that catch can move out of the catch recess 55.

At the end of the shuttle 19 nearest to the opening 4 a lip 56 of the shuttle catch 23 locates over a shoulder 57 on the base 2. Upon rotating of the support 7 together with the nozzle unit 6 out of the case, and upon removal of the cap 40, the shuttle catch 23 is pressed down so lifting the lip 57 away from the shoulder 56. This is described in more detail below with reference to FIG. 6a.

In the sectional view of FIG. 5a are also seen the internal component parts of the nozzle unit 6. As described in more detail in EP-A-0546607 there is a piston member 71 in which is mounted a hollow needle 72. Held within the vial holder 43 is a vial 73 closed by a rubber stopper 74. The hollow needle 72 is in alignment with the nozzle opening 50. Upon depression of the vial holder 43, the needle 72 pierces the rubber stopper 74 and the stopper is pushed along the vial 73 by the piston member 71, thus expelling all of the contents through the needle and thus through the nozzle opening.

Figure 5B:
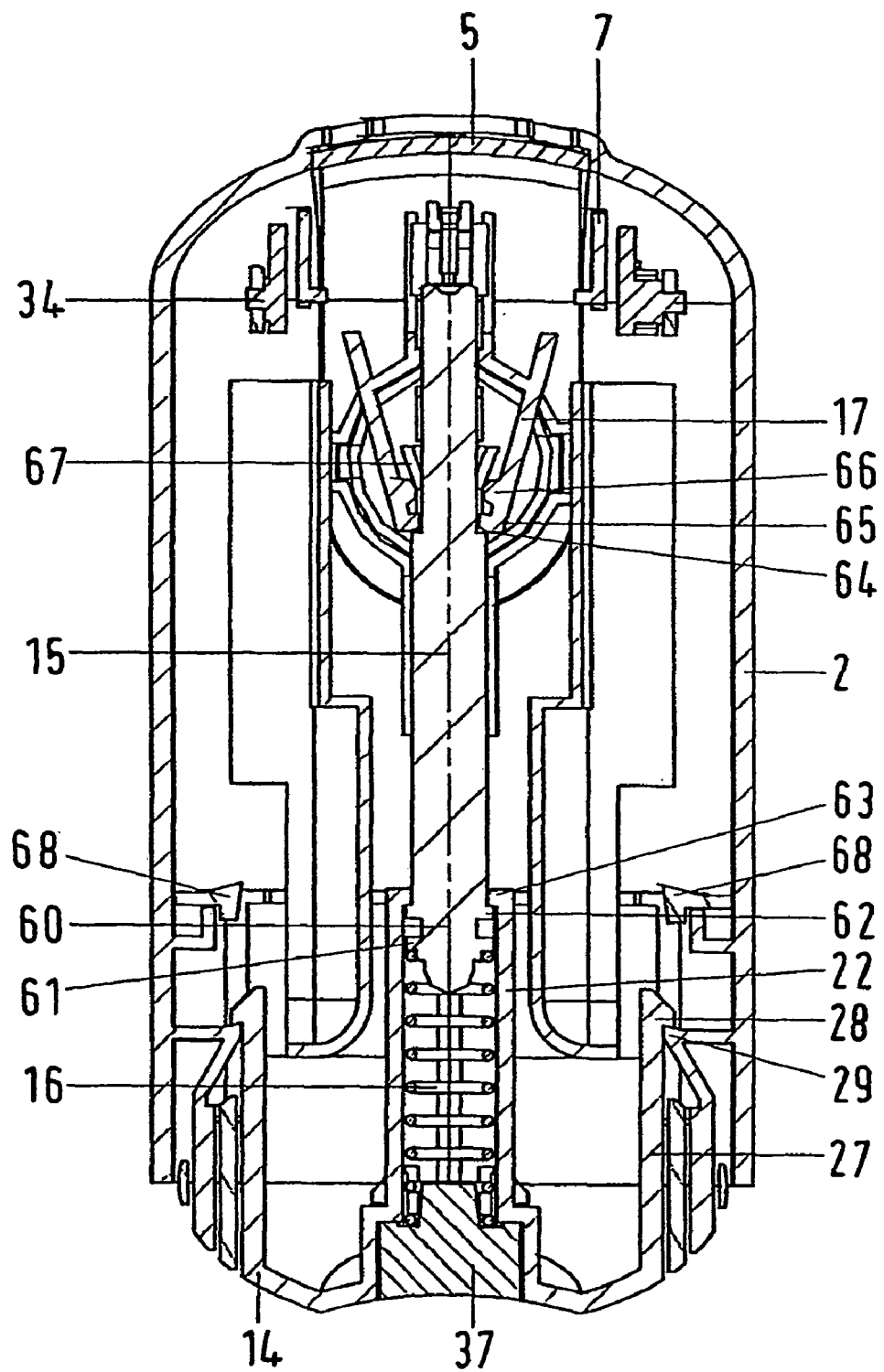

The horizontal sectional view of FIG. 5b shows more clearly the mounting of the carriage 14 and piston member 15 on the base 2. As already mentioned, the carriage 14 can slide along the base from the rearward position shown in FIG. 5b to a forward position. In the rearward position the hook catches 28 of the arms 27 of the carriage 14 locate over the shoulders 29 of the base. It will be noted that similar shoulders 68 are provided on the inside of the cover 3, in a more forward position relative to the carriage, and when the cover is closed on the base of the shoulders 68 provide an advanced position for the catches 28 (these shoulders 68 of the cover can also be seen in FIG. 2).

The piston member 15 is mounted on the carriage 14 through piston housing 26. At the rearward end of the piston there are two annular shoulders 61 and 62. Piston spring 16 is located against the shoulder 61, the other end of the spring being located against the inner end of the plug 37 which is force fitted into the rearward end of the carriage. The other, more forward shoulder 62 abuts an annular lip 63 of the carriage housing 26, thus preventing the piston member from moving further out of the housing 26.

FIG. 5b also shows in more detail the blocking of the piston rod 15 by the resilient arms 17 which are mounted on the base 2. At their rearward ends, the spring arms 17 have lugs 64 which engage against an annular shoulder 65 of the piston rod 15. Rounded portions 66 on the inside of the spring leg 17 rest against inclined surfaces 67 of the shuttle 19. The cooperation of the shuttle 19 and spring arms 17 will be described in more detail below, but it is evident from FIG. 5b that the piston rod 15 cannot move to a more forward position until such time as the resilient arms 17 are opened.

Figure 6A:
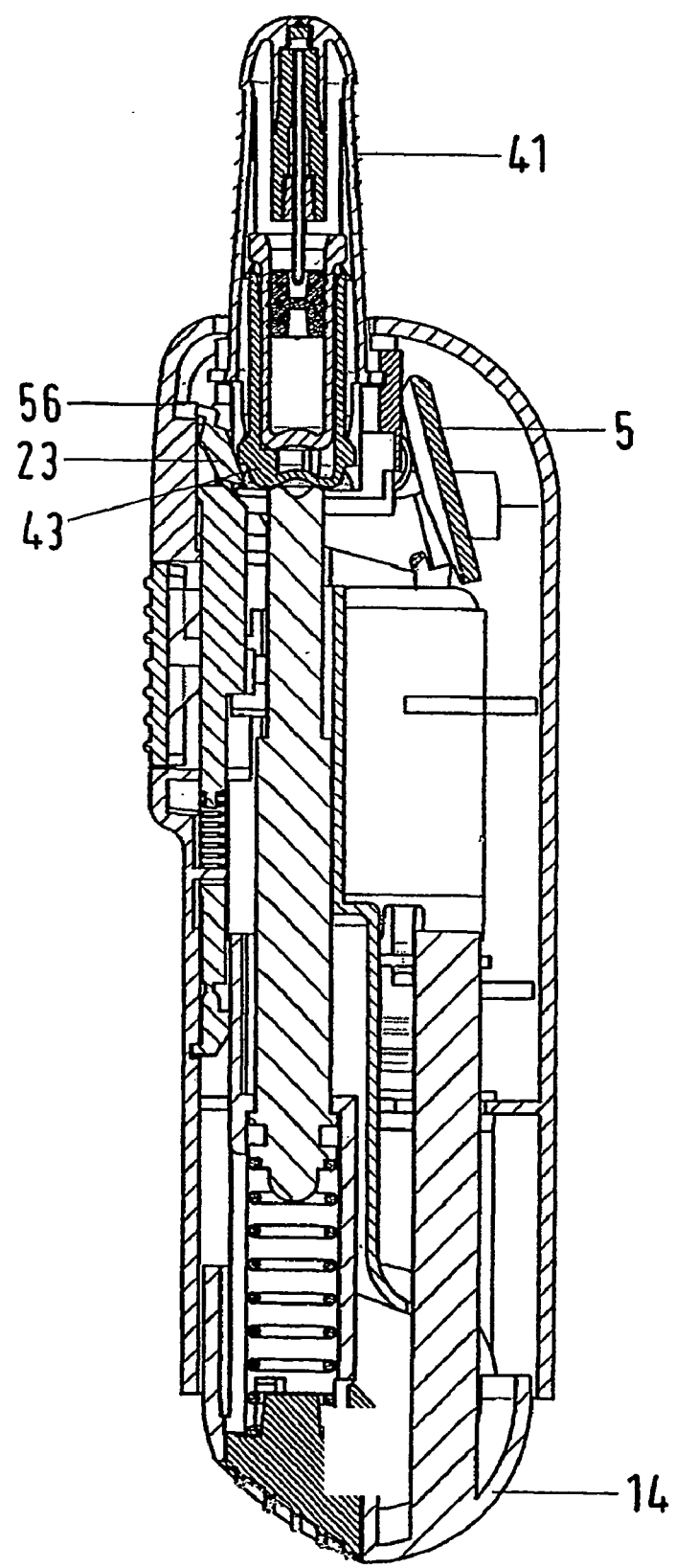
FIGS. 6a and 6b are sectional views similar to those of FIGS. 5a and 5b, but showing the unit containing the pharmaceutical substance in its outer position, ready-to-use.
Figure 6B:
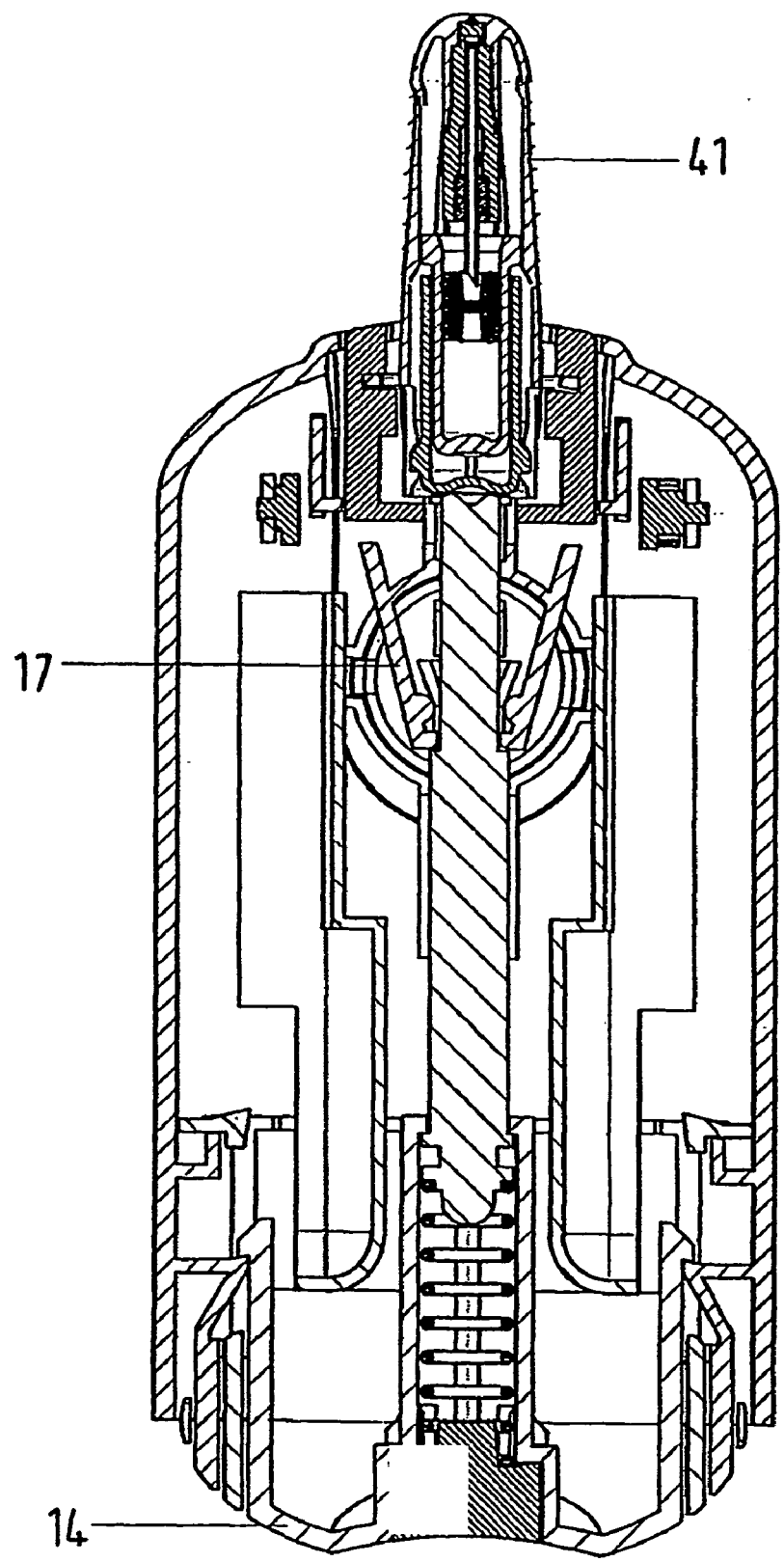

The sectional views of FIGS. 6a and 6b are similar to those of FIGS. 5a and 5b, but these Figures show the device in a ready-to-use state. The nozzle member 41 is positioned outside of the device so that it can be inserted into the user's nasal cavity. To arrive at this position, the cover 3 must be opened and the nozzle unit 6 pivoted outwardly on the support 7. After pivoting out of the nozzle unit, the cap 40 is removed and the cover 3 is closed again. The closing action of the cover forces the lid 5 against the support 7 and the lid 5 is pivoted inside the cover 3, against the action of the lid spring 36. In the outward position of the nozzle member 41 the outer end of the vial holder 43 is immediately adjacent the forward end of the piston member 15. The nozzle member is firmly held in place on the support 7 by the edges of the opening 4 of the base.

Upon previous mounting of the nozzle unit on the support 7 the inclined surfaces 76 on the inside of the support 7 have acted against the cap wings 44, thus moving the cap wing catches 45 into a position at which they can move through the skirt openings 48 of the nozzle member 41. In other words, correct mounting of the nozzle unit 6 on the support 7 automatically releases the locking engagement of the cap 40 on the nozzle member 41. Thus, the cap 40 can easily be removed from the nozzle unit 6 when the nozzle unit is pivoted away from the base. Until such time as the cap 40 is removed, the nozzle member 41 cannot be moved to the position shown in FIG. 6a, in alignment with the piston rod 15, because the cap 40 is wider than the nozzle member 41 and would abut the edge of the opening 4. Equally, until the cap 40 is removed the cover 3 cannot close on the base 2, as the nozzle unit would be blocking the final engagement of the cover on the base.

It will be seen from FIG. 6a that when the nozzle member 41 is correctly positioned, pivoted outwardly of the base, then the shuttle catch 23 locates in the gaps between the skirt arms 47 of the nozzle member 41, thus allowing the vial holder 43 to press the catch 23. The shuttle catch 23 is arranged at the end of the shuttle 19 on a "living hinge" and a force on the inclined surface of the shuttle catch 23 acts to pivot the lip 56 off the shoulder 57 of the base 2. It can be noted at this stage that if an already used nozzle member were mounted, then the vial holder 43 would be at an advanced position within the nozzle member 41 and could not, therefore, contact the shuttle catch 23 to release it.

To bring the device shown in FIGS. 6a and 6b into an actuation condition, it is necessary to advance the carriage 14 along the base 2. This is done by the user pushing the carriage 14 into the device, for example by means of thumb pressure on the surface of the plug 37.

Figure 7A:
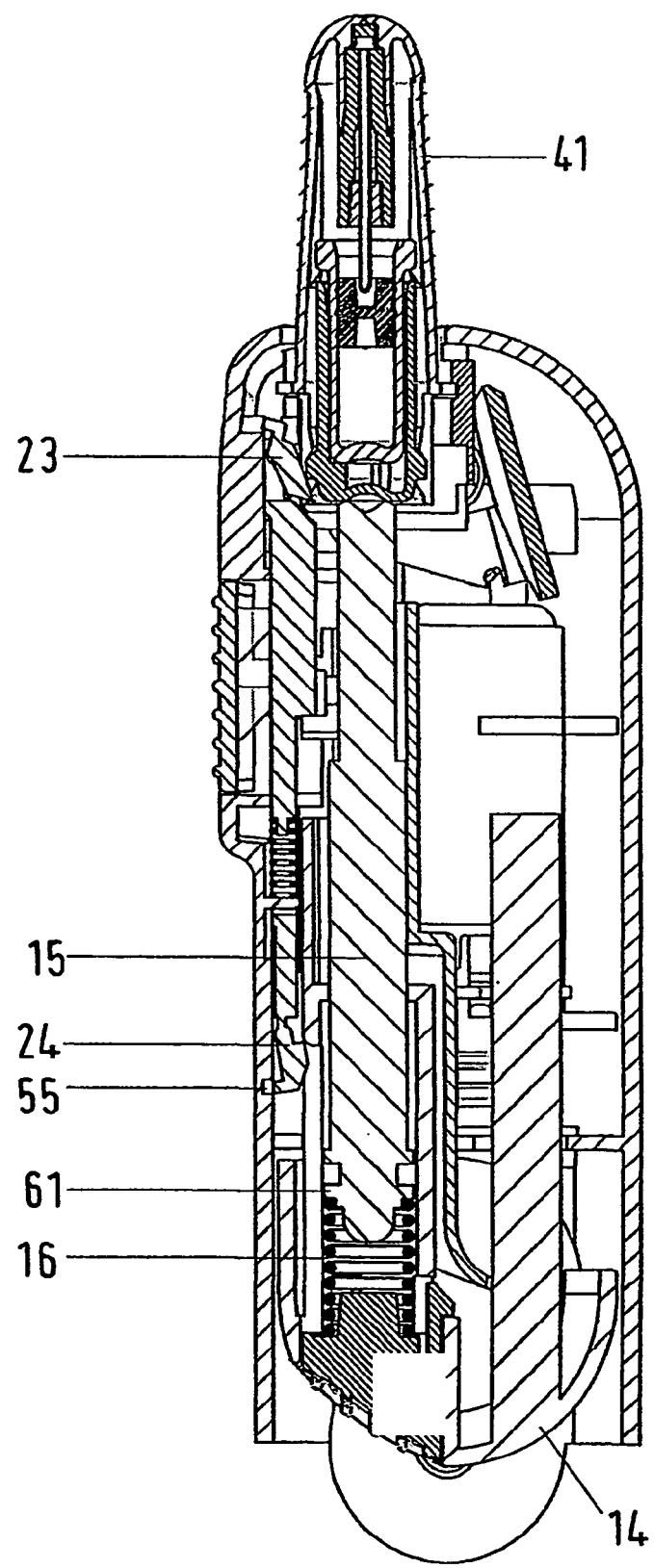
FIGS. 7a and 7b are similar sectional views, showing the device in a primed condition.
Figure 7B:
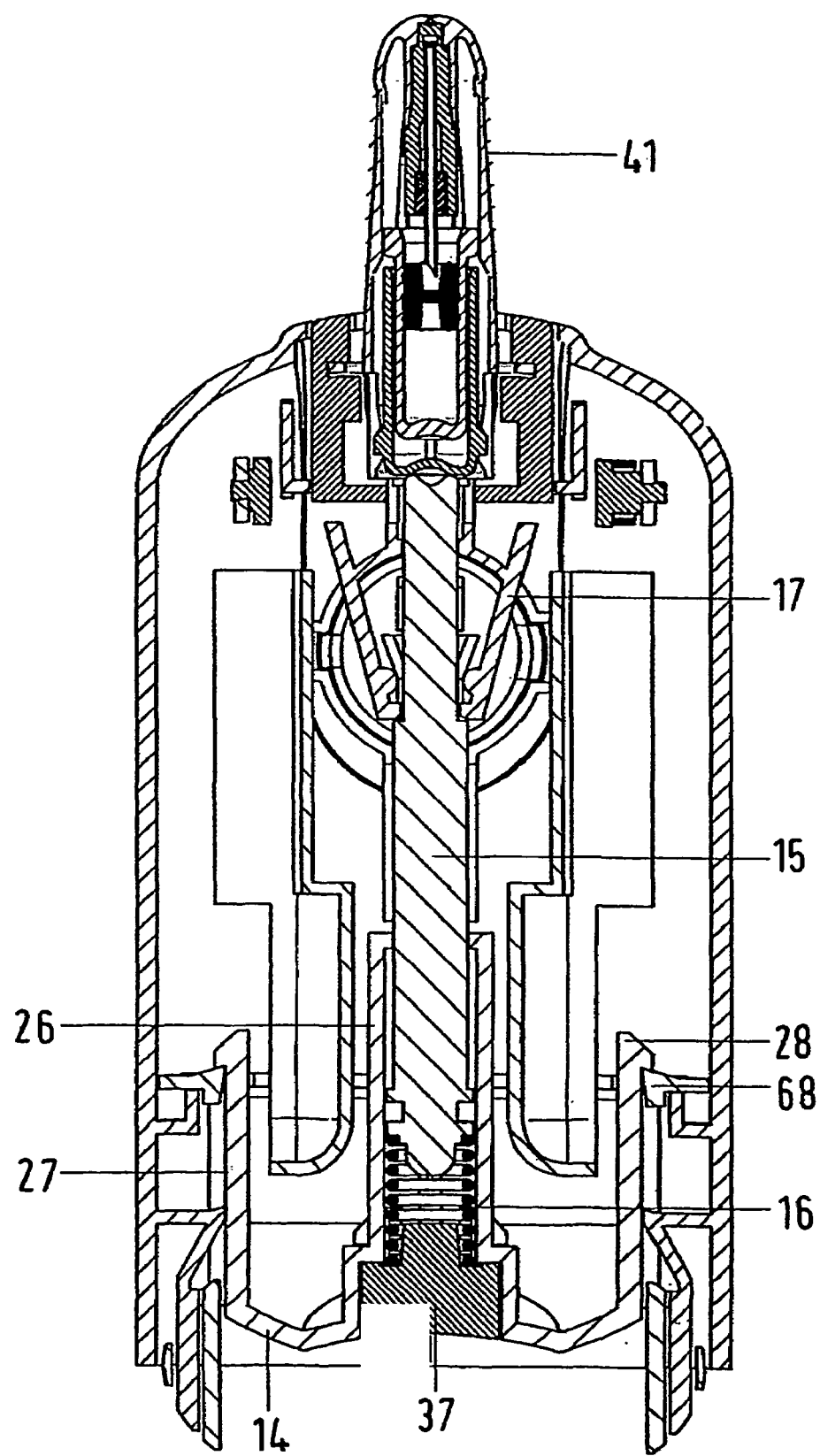

The advanced position of the carriage 4 is shown in FIGS. 7a and 7b. From FIG. 7b, it can be appreciated that carriage 14 is advanced to a forward position in which the carriage hooks 28 engage over the shoulders 68 on the inside of the cover 3. The carriage arms 27 have a sufficient degree of resiliency to allow the hooks 28 to pass the shoulders 68, before snapping outwardly to engage over the shoulders 68.

As the piston member 15 remains blocked by the resilient arms 17 on the base 2, on the advancement of the carriage 14, the piston housing 26 moves along the piston member 15 and the piston spring 16 is compressed between annular shoulder 61 of the piston member 15 and the inside of the plug 37. In the advanced position of the carriage 14, the open portion 54 of the piston housing 26 registers with the catch 24 of the shuttle 19, thus allowing the catch 24 to disengage from the catch hole 55 in the base 2.

In the condition seen in FIGS. 7a and 7b, both safety catches 23 and 24 of the shuttle 19 are released from the base 2, leaving the shuttle 19 in a condition in which it is able to move along the base 2, against the action of shuttle spring 22.

Figure 8A:
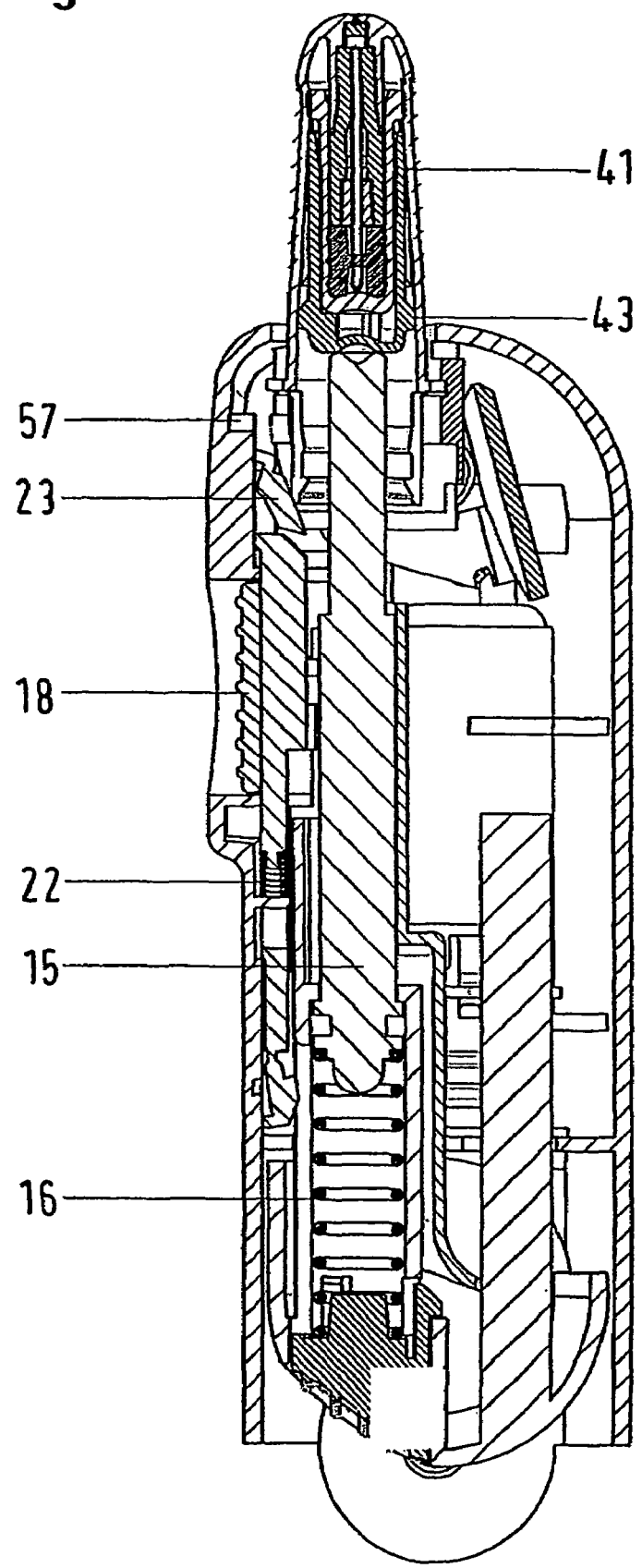
FIGS. 8a and 8b are similar sectional views showing the device in a used condition, with the pharmaceutical substance having been dispensed.
Figure 8B:
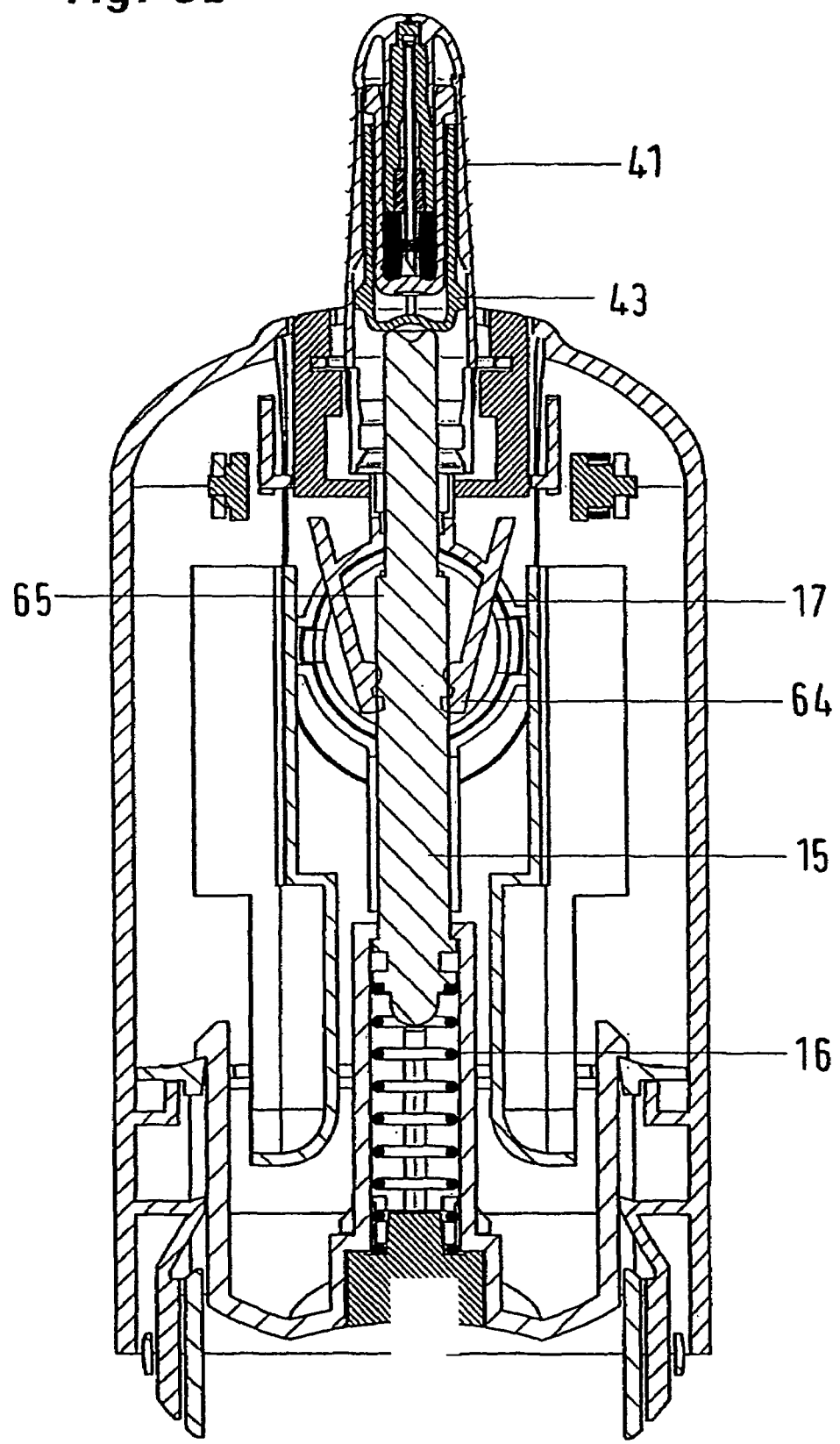

FIGS. 8a and 8b show the condition of the device wherein the button 18 has been depressed, the resilient arms 17 opened and thus the piston rod 15 released. The cooperation of the button 18 with the shuttle 19 and the resilient arms 17 is described in detail below with reference to FIGS. 9a and 9b.

Upon opening of the resilient arms 17, the lugs 64 move away from the shoulder 65 of the piston rod is. As soon as the resilient arms 17 are clear of the piston rod 15, the force of the piston spring 16 urges the piston rod 15 forwardly, immediately pushing the vial holder 43 into the nozzle member 41. In the same way in which the pharmaceutical substance is dispensed in prior application EP-A-0546607, movement of the vial holder 43 within the nozzle member 41 in the present device causes the contained pharmaceutical substance to be sprayed out of the nozzle opening 50 into the user's nasal cavity.

Of course, for delivery of the pharmaceutical substance, the user places the device in such a position that the nozzle member 41 is in one of the nasal cavities, the device being held in the hand with the thumb over the button 18.

Upon release of the button 18 (i.e. when the button moves to the left in FIG. 8a) the shuttle spring 22 will move the shuttle 19 in a forward direction so that the shuttle catch 23 is again engaged with the base 2. It is seen from FIG. 8a that with the vial holder 43 advanced within the nozzle member 41 the shuttle catch 23 is allowed to assume its position engaged behind the shoulder 57 of base 2.

Figure 9A:
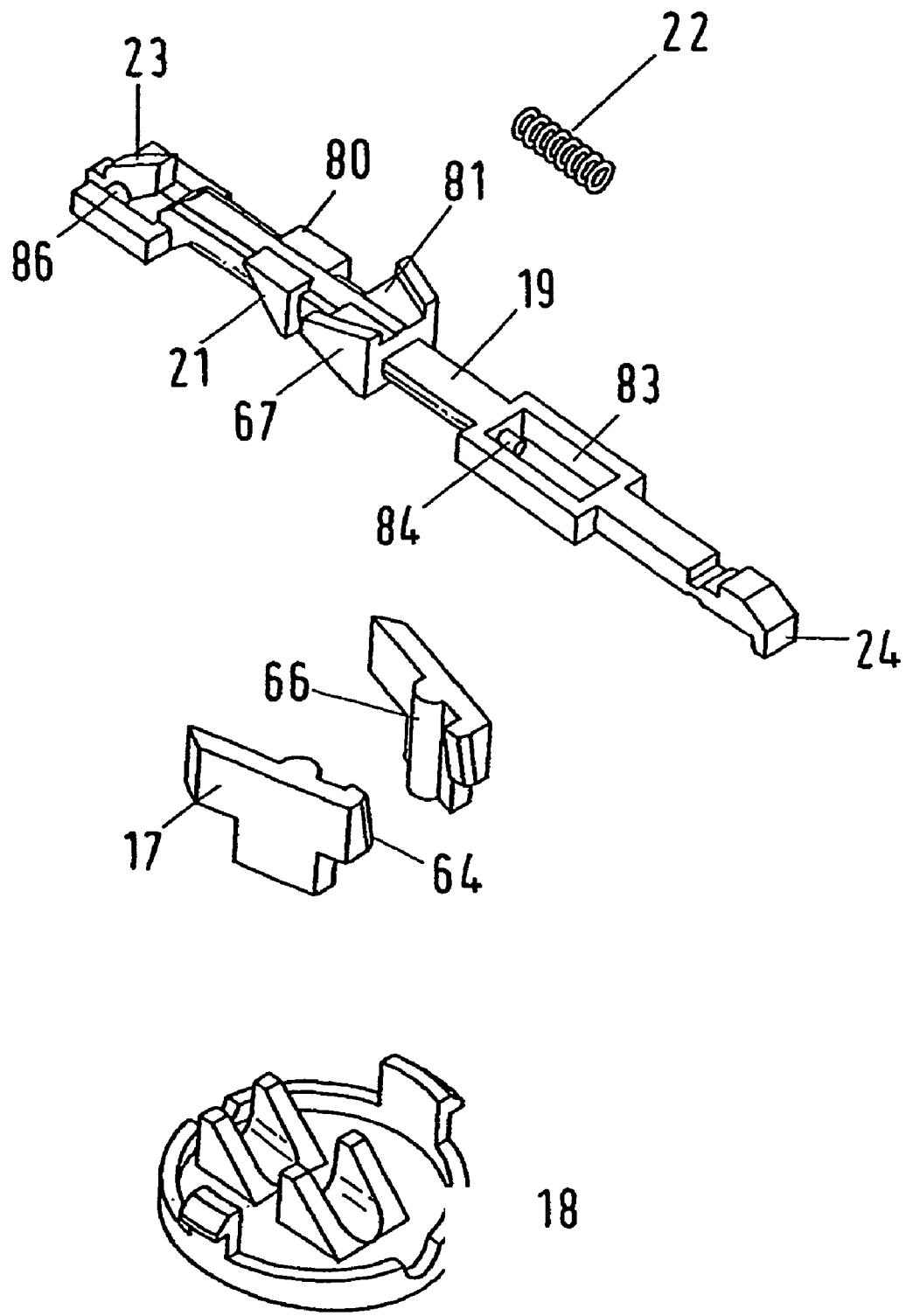
FIGS. 9a and 9b are perspective views from above and from below showing in detail the operation of the release mechanism of the device.
Figure 9B:
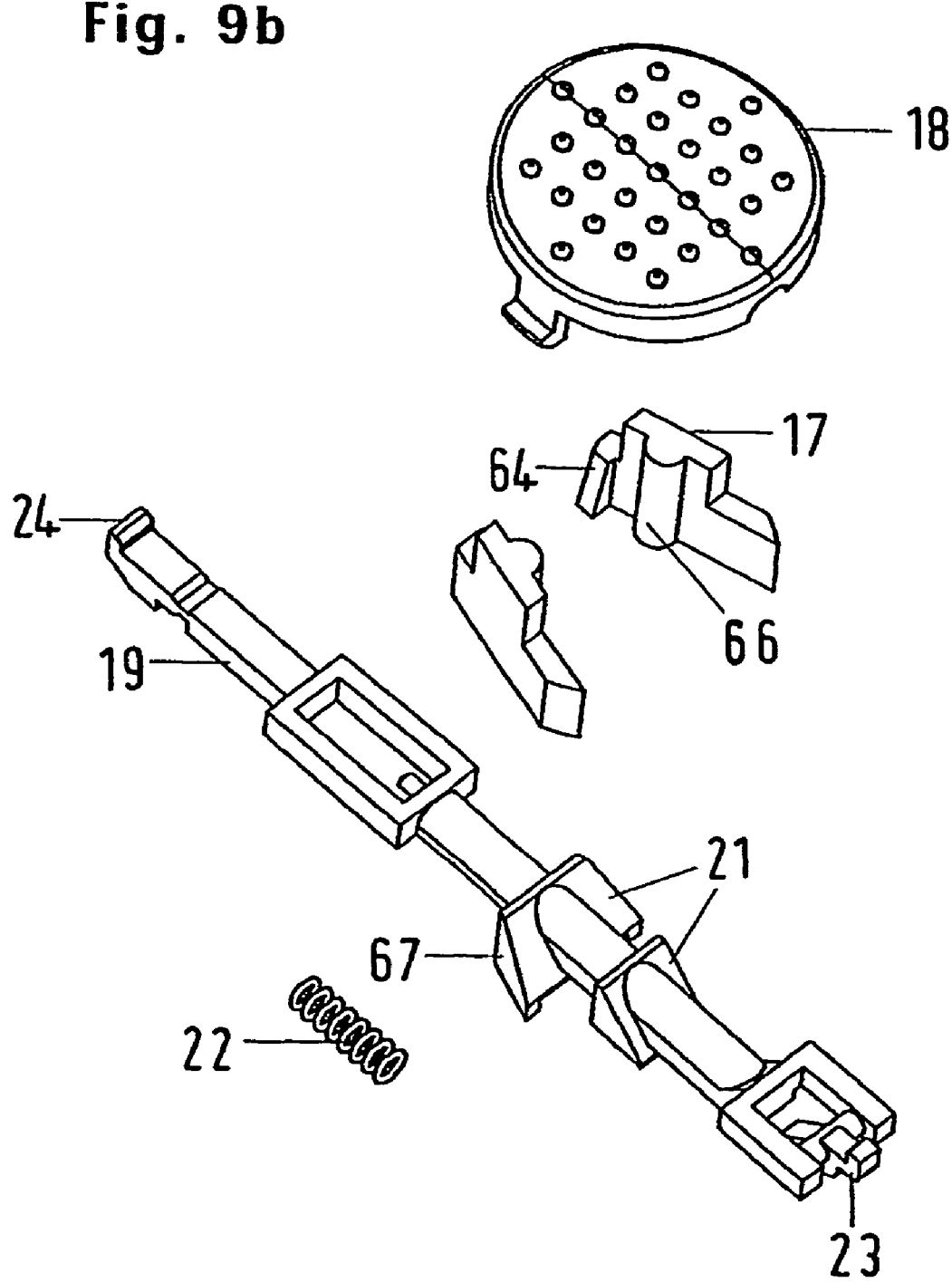

As indicated above, FIGS. 9a and 9b show the cooperation between the button 18, the shuttle 19 and the arms 17 of the base 2. The perspective views of FIGS. 9a and 9b are from opposite sides, so that both top and bottom surfaces of the relevant parts can be seen.

Button 18 is of a generally circular configuration and is clipped into a correspondingly shaped aperture in base 2. On the inside surface of the button 18 there are two sets of two inclined surfaces 20 which are for sliding engagement with correspondingly inclined surfaces 21 on the shuttle 19. The surfaces 21 are formed on integrally moulded blocks 80, 81 along the length of the shuttle 19. The block 81 nearest to shuttle catch 24 includes the lateral inclined surfaces 67 which are bevelled outwardly, away from the shuttle catch 24 end.

Between this block 81 and the shuttle catch 24 is formed a rectangular opening 83 including a pin 84 for location of the shuttle spring 22. On assembly of the shuttle 19 to the base 21 the rectangular 83 opening fits over an internal lip 85 of the base 2 (see. FIG. 5a for example), with the shuttle spring 22 abutting against the lip 85.

Upon movement of the button upwardly as seen in FIG. 9a, or downwardly as seen in FIG. 9b, the inclined surfaces 20 of the button move against the correspondingly inclined surfaces 21 of the shuttle 19, thus forcing the shuttle to the right in FIG. 9a, i.e. rearwardly in the device. This movement in turn pushes the lateral inclined surfaces of the block of the shuttle 19 along the rounded portions 66 of the resilient arms 17, forcing the arms 17 to open and releasing the lugs 64 from the shoulder 65 of the piston arm is.

FIGS. 9a and 9b clearly show the safety catch 23, including the living hinge 86 connecting the catch to the shuttle 19.

After actuation of the device, the used nozzle member 41 will need to be disposed of. To remove the nozzle member, the cover 3 is opened, the support 7 pivoted back inside the base 2 and the used nozzle member 41 removed for safe disposal.

FIGS. 10a to 10e show how the opening of the cover 3 retracts the carriage 14 to its rearward position. As briefly mentioned in relation to FIG. 3, a pin 31 on each side of the pivoting end of the cover 3 cooperates with a cam track 30 on the sides of the carriage 14. At the base side of the track, there is a straight portion 90 which is parallel to the direction of movement of the carriage 14 along the base 2. At the forward end of this straight portion there is an arcuate portion 91 extending back around approximately 180°. From the rearward end of the straight portion a slightly curved portion 92 extends to intersect the arcuate portion 91 approximately ¾ of the way along its length from the forward end of the straight portion 90.

Figure 10:
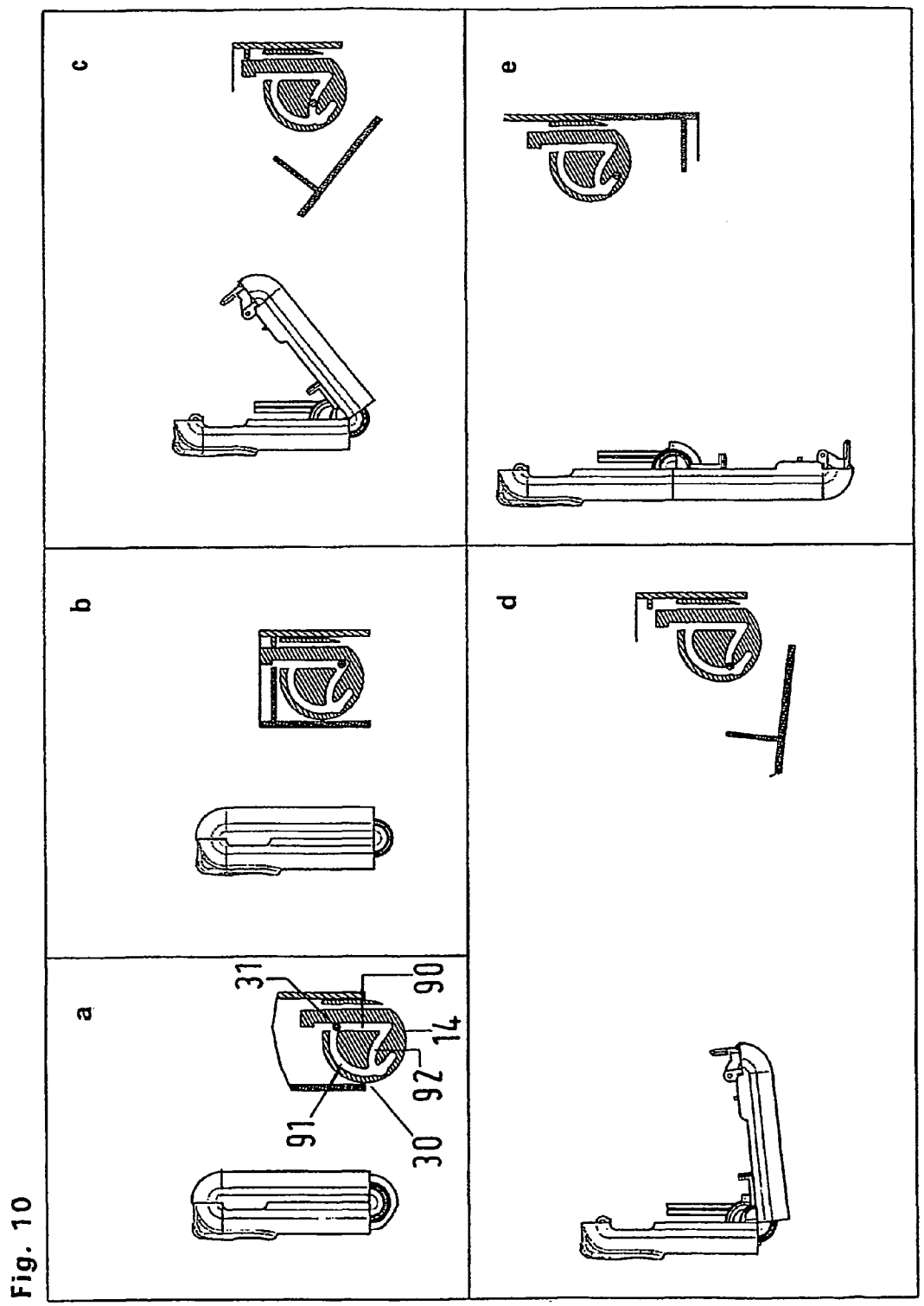
FIGS. 10a to 10e are detail sectional views showing the movement of parts of the device as the base and cover are moved relative to one another.

FIG. 10a shows the cover closed 3 on the base 2, with the carriage 14 in its normal, rearward position. Here the pin 31 is located at the forward end of the straight portion 90 of the track 30. It is clear that upon opening and closing of the cover 3, the pivotal movement of the cover will move the pin 31 along the arcuate portion 91. With 180° opening of the cover 3, the pin 31 will of course arrive at the opposite end of the arcuate track 91.

FIG. 10b shows the carriage 4 in its advanced position, i.e. in a position shown in FIGS. 7a and 7b. With the forward movement of the carriage 14 along the base 2, the pin 31 moves relative to the carriage 14 such that it is located at the rearward end of the straight portion 90 of the track. After actuation of the device and opening of the cover 3, it is seen in FIG. 10c that the pin is forced along the inclined portion 92 which acts as a cam surface. Thus, pivoting of the cover 3 forces the pin to retract the carriage 14.

The retracted position of the carriage is seen in FIG. 10d. For completeness, it is noted at this point that opening of the cover disengages the shoulders 68 of the cover from the hooks 28 of the carriage, freeing the carriage to move back to its initial position. Upon full retraction of the carriage 14 the pin 31 is able to move to the end of the arcuate portion 91 of the track, should full 180° opening of the cover be desired by the user. This condition is seen in FIG. 10e.

Whether the cover 3 is moved back to the closed position from the state seen in FIG. 10d or the state seen in FIG. 10e, it will be understood that upon pivoting of the cover 3 relative to the base 2 the pin 31 will travel back around the arcuate portion 91 of the cam track 30 to the position shown in FIG. 10a. In this condition, the cover 3 is closed and the carriage 14 is again in its rearward position.

Having described the construction of the device for administering a pharmaceutical substance in accordance with this embodiment of the invention, the way the device is intended to be used will now be described (though many of the aspects of the operation of the device will already have been understood from the above description of the device and the interaction of the different parts thereof).

In the normal situation, the user will start with a closed device, with an unused nozzle unit 6 mounted on the support 7 and folded onto the base 2 with the cover 3 folded down thereover. In other words, in the normal start condition the device will be in the condition seen, in FIGS. 1 and 5.

If it is assumed that the pharmaceutical substance contained in the nozzle unit is Sumatriptan then the device will be used for the alleviation of the symptoms of a migraine. On sensing the onset of a migraine attack, the user will lift the cover 3 of the device and fold out the nozzle unit 6. Previous mounting of the nozzle unit on the support 7 will have disengaged the catches on the cap 40 of the nozzle unit 6. Thus, the user can easily remove the cap 40 so that the nozzle member is ready for location in the nasal cavity. After removal of the cap 40, the cover 3 is closed back onto the base 2. If the support, 7 has not already be pivoted out to its full extent, the closure of the cover 3 on the base 2 will complete the movement of the support 7, and thus the nozzle member 41, so that the nozzle member 41 is correctly aligned with the piston rod 15. This condition is seen in FIGS. 6a and 6b.

As already mentioned above, pivoting of the nozzle unit out to its full extent releases the forward catch 23 of the shuttle 19. In this position, the device is ready to be brought into an actuation condition by the user. To achieve this, and thus to cock the spring 16 which drives the piston rod 15, the user presses the carriage 14 into the device, thus forcing the carriage 14 to slide along the base in a direction towards the nozzle unit. As the piston rod 15 is blocked by the spring arms 17, the piston housing 26 of the carriage 14 slides relative to the piston rod 15, thus compressing the piston spring 16. In the advanced position of the carriage 14, the catches 28 on the carriage arms 27 locate over the forward shoulders 68 of the cover 3. With the carriage in the advanced position, the rearward catch 24 of the shuttle 19 has disengaged from the base 2. This position of the carriage is seen most clearly in FIG. 7b.

The device is now ready to be operated by the user in order to deliver a predetermined dose of the pharmaceutical substance. The device is held in the user's hand, with the nozzle member correctly located in the nasal cavity and the button 18 is depressed. Depression of the button 18 forces the shuttle 19 to slide in a rearward direction, the lateral inclined surfaces 67 of the shuttle 19 opening the arms 17 of the base. With the arms 17 separated, the piston rod 15 is released so that under the force of the spring 16 it drives the vial holder 43 into the nozzle member 41. Thus, the pharmaceutical substance is delivered to the user, in the same manner as described in prior application EP-A-0546607.

With the spring 16 having a predetermined resilient force, the piston rod 15 will be driven with a predetermined and relatively constant force, so that a very reliable expulsion of the substance out of the nozzle opening 50 will be achieved. The condition of the device with the piston rod released and the substance dispensed is shown in FIGS. 8a and 8b.

At this stage the actions of any individual user cannot be predicted, in that if someone is suffering from a severe migraine attack they may at this point simply put the device down and only deal with it when the attack is over, or at least the symptoms have been greatly alleviated. However, after actuation, the user will ideally open the cover, fold in the used nozzle member 41 and remove that nozzle member for disposal. The cover can of course be closed again at this point, but it is preferable for a replacement nozzle unit 6 to be located in the support 7, so that the device will be immediately ready for use at a later date. A spare nozzle unit will be present on the inside of the cover 3 and that spare unit can itself be replaced by another unit.

As discussed in particular in relation to FIGS. 10a to 10e, the opening of the cover 3, after administration of the pharmaceutical substance, automatically brings the carriage 14 back to its rearward position. Thus, on mounting a replacement nozzle unit and again closing the cover, the device is again in a ready-to-use condition, as seen in FIGS. 5a and 5b. It is thus understood that the device is easy to use and can be operated in a reliable and straightforward fashion to quickly and efficiently dispense a dose of pharmaceutical substance, as the need arises.

It will also be appreciated that the device includes several security features to ensure that the device is operated in the intended fashion. In particular, the following features are included.

1. The cover joins with the base by means of a child proof closure. Only by applying inward pressure to the sides of the cover at the appropriate point can the device be opened.
2. The cap of the nozzle unit can only easily be removed upon mounting of the nozzle unit on the support. Thus, the cap protects the nozzle itself from contamination, prior to use (the pharmaceutical itself, inside the nozzle member, is sealed inside the vial, until such time as the stopper is punctured by the needle). The cap also acts as a tamper evident feature, so that the user can immediately see if a nozzle member has already been used. In other words, the user will only try and administer the pharmaceutical substance from a nozzle unit which has a cap correctly in place.
3. The cap cannot be removed from the nozzle unit until the support is pivoted to the outward position. Thus, the cap cannot be inadvertently removed after initial mounting of the nozzle unit on the support with the support still folded inwardly of the base.
4. The piston spring cannot be cocked until the device is in a ready-to-use condition. In particular, until the nozzle unit is pivoted out, the carriage is blocked by the nozzle unit mounted on the support. Similarly, there is no possibility of cocking the spring when the case is open as the carriage cannot be engaged in a forward position until the shoulders 68 of the cover are adjacent the base.
5. The cover cannot be closed onto base until the cap is removed from the nozzle unit which has already been pivoted out from the base. Thus, there is no possibility of the user trying to administer the pharmaceutical substance without first removing the cap from the nozzle member.
6. Only with the cap removed from the nozzle unit can the nozzle member be fully pivoted out from the base and only in the fully pivoted position will the vial holder release the forward catch of the shuttle. Thus, the shuttle is locked against movement until a nozzle unit with the cap removed is pivoted out.
7. If the user tries to activate the device with an already used nozzle member, then the vial holder will be in such a forward position that it does not release the catch of the shuttle. Thus, the user cannot reuse a nozzle member. Similarly, if no nozzle member at all is present the shuttle catch remains locked against the base.
8. The rearward shuttle catch remains locked against the base until such time as the carriage is in its forward position. This prevents the piston rod from being released by pressure on the button until such time as the piston spring is properly compressed. Thus, reliable dispensing of the pharmaceutical substance within the nozzle member is ensured.
9. The nozzle units themselves are protected against accidental actuation by virtue of the fact that the skirt legs of the nozzle member surround the vial holder, so that upon handling of the nozzle unit the vial holder is not accidentally pushed into the nozzle member by the user's fingers or thumb.

The component parts of the device described above are moulded from a suitable plastics material. For example, the base, cover and support can be made of ABS (Acrylonitrile Butadiene Styrene) or polycarbonate (PC). The carriage, button and plug can similarly be made of PC, while the piston and shuttle might be made of polyoxymethylene (POM). The springs are made of steel.

The invention claimed is:

1. A device for dispensing a pharmaceutical substance comprising:
    a base member and a cover member closeable thereon;
    a dispensing member which is movable between a first position on the base member under the closed cover member and a second position protruding from the base member after opening and redo sing of the cover member;
    a container of the pharmaceutical substance to be dispensed; and
    an actuating member for discharging the pharmaceutical substance from the container and through the dispensing member;
    wherein in the first position of the dispensing member the container is not in registration with the actuating member so that a release member can cause dispensing of the pharmaceutical substance through the dispensing member; and
    wherein in the second position of the dispensing member the container is in registration with the actuating member so that the release member can cause dispensing of the pharmaceutical substance through the dispensing member.

2. A device according to claim 1, wherein the dispensing member is pivotable relative to the base between the first and second position.

3. A device according to claim 2, wherein the dispensing member is mounted on a support which is pivotally connected to the base.

4. A device according to claim 3, wherein the dispensing member has a protective cap which has locking wings to hold it on the dispensing member, the pivotal support having surfaces which retract the locking wings upon mounting of the dispensing member on the support.

5. A device according to claim 4, wherein the base member has an edge surface which prevents registration of the dispensing member with the actuating member until removal of the protective cap.

6. A device according to claim 3, wherein the dispensing member is slidable onto and off of the pivotal support.

7. A device according to claim 1, wherein the actuating member has a primed condition and an unprimed condition, the primed condition being achieved by sliding movement of a carriage on the base member.

8. A device according to claim 7, wherein the cover member cooperates with the carriage such that after dispensing, opening of the cover member slides back the carnage to its initial position.

9. A device according to claim 8, wherein a pin on the cover cooperates with a cam track on the carriage.

10. A device according to claim 7, wherein the carriage includes a surface which is blocked by the dispensing member in its first position, thus preventing movement of the carriage.

11. A device according to claim 10, wherein the surface is at the end of an arm of the carriage.

12. A device according to claim 7, wherein the carriage and dispensing member are provided at opposite ends of the base member, the carriage being slidable in a direction towards the dispensing member in its second position, the actuating member comprising a piston rod arranged between the carriage and the dispending member.

13. A device according to claim 12, wherein the release member is elongate and is arranged on the base parallel to the piston rod, the safety catches of the release member being at opposite ends thereof and the push button being moveable perpendicularly to the release member.

14. A device according to claim 7, wherein sliding of the carriage compresses a spring which is released by the release member to actuate the actuating member.

15. A device according to claim 7, wherein the safety member has a second safety catch which holds it in position on the base, the second safety catch being released upon sliding movement of the carriage.

16. A device according to claim 7, wherein the carriage can be held in a forward condition on the base by means of catch surfaces on the cover.

17. A device according to claim 1, wherein the dispensing member is removable from the base member for disposal after use.

18. A device according to claim 17, wherein two or more spare dispensing members are mounted on the base or cover member.

19. A device according to claim 1, wherein a push button on the base or cover member is configured to move the release member, with inclined surfaces on the release member being configured to move catches on the base member which hold the actuating member.

20. A device according to claim 19, wherein the catches of the base member are at the ends of resilient arms.

21. A device according to claim 1, wherein the dispensing member includes the container.

22. A device according to claim 1, wherein the release member has at least a first safety catch which holds it in position on the base, the first safety catch being released by movement of the dispensing member to the second position.

23. A device according to claim 1, wherein the dispensing member is nozzle shaped for insertion in a nasal cavity.

* * * * *